United States Patent [19]

Perkins

[11] 4,071,028
[45] Jan. 31, 1978

[54] RADIO FREQUENCY CAUTERY INSTRUMENT AND CONTROL UNIT THEREFOR

[76] Inventor: George C. Perkins, 5809 Braniff Drive, Oklahoma City, Okla. 73105

[21] Appl. No.: 658,598

[22] Filed: Feb. 17, 1976

[51] Int. Cl.² .................... A61B 17/36; A61N 3/02
[52] U.S. Cl. .................... 128/303.14; 128/303.17; 307/117; 307/252 B
[58] Field of Search .................... 128/303.13, 303.14, 128/303.15, 303.16, 303.17, 303.18, 2.1 P; 307/117, 252 B, 311

[56] References Cited

U.S. PATENT DOCUMENTS

| 3,395,333 | 7/1968 | Aiken | 307/311 X |
| 3,663,838 | 5/1972 | Reimers | 307/311 |
| 3,699,967 | 10/1972 | Anderson | 128/303.14 |
| 3,801,800 | 4/1974 | Newton | 128/303.14 X |

FOREIGN PATENT DOCUMENTS

| 16,747 | 11/1966 | Japan | 307/117 |
| 145,908 | 7/1962 | U.S.S.R. | 307/311 |

OTHER PUBLICATIONS

Popular Electronics, vol. 35, No. 2, Aug. 1971, p. 88.
French, "L.E.D. -L.D.R. Isolator", Radio & Electronics Constructor, Apr. 1975, pp. 532-534.

Primary Examiner—Ronald L. Frinks
Assistant Examiner—Lee S. Cohen
Attorney, Agent, or Firm—William R. Laney

[57] ABSTRACT

An improved radio frequency cautery instrument comprising a radio frequency signal generator for supplying both monopolar and bipolar radio frequency signal outputs for medical applications. A control unit is interposed between the radio frequency outputs of the signal generator and the hand-held electrode assembly, and further interposed between a finger-operated switch on the electrode assembly and the power circuit of the signal generator, whereby the application of radio frequency energy to the electrode of the electrode assembly can be controlled by the user through manipulation of the finger-operated switch on the electrode assembly.

13 Claims, 8 Drawing Figures

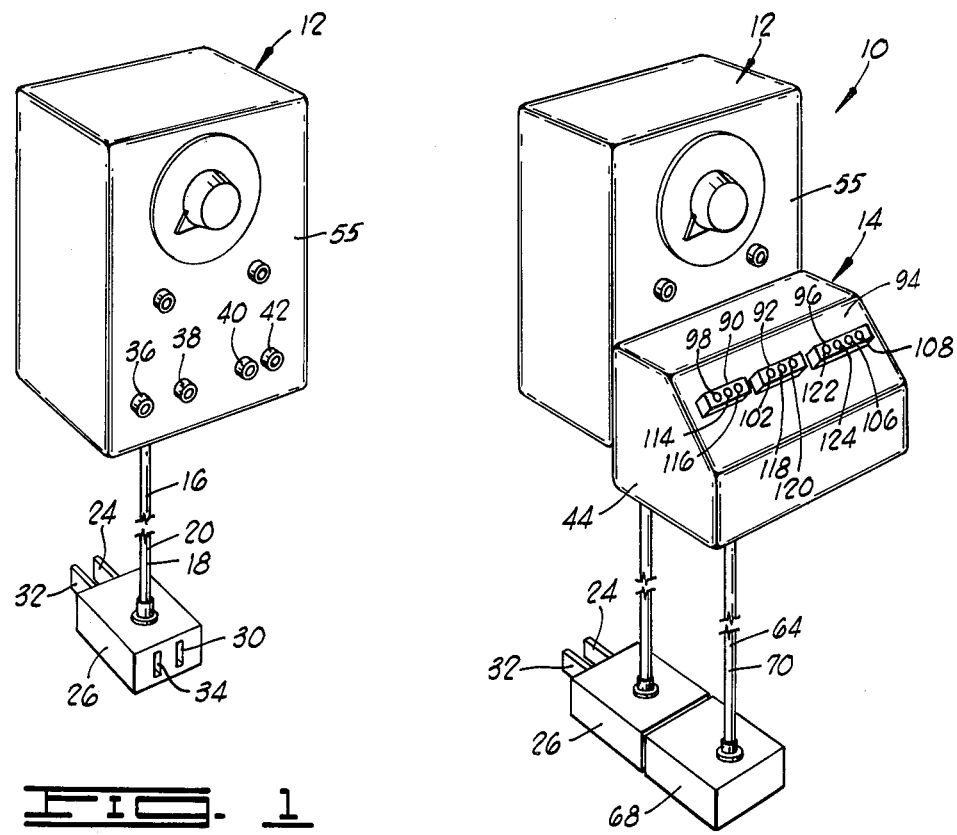
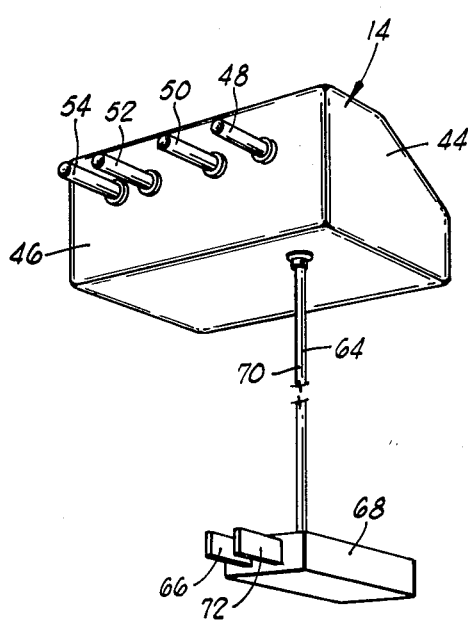
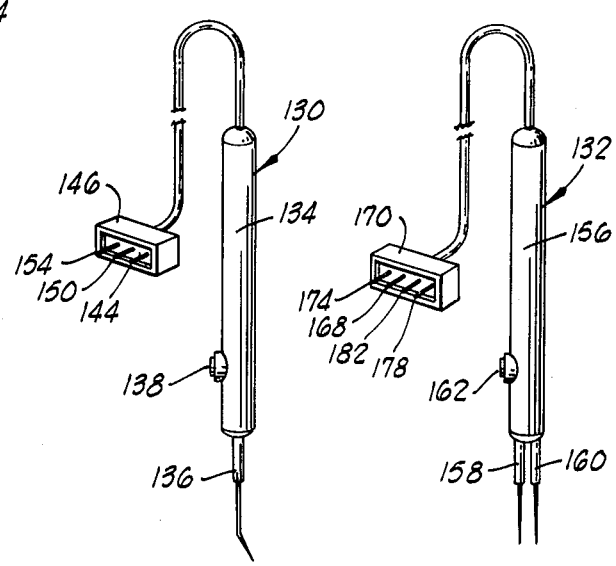

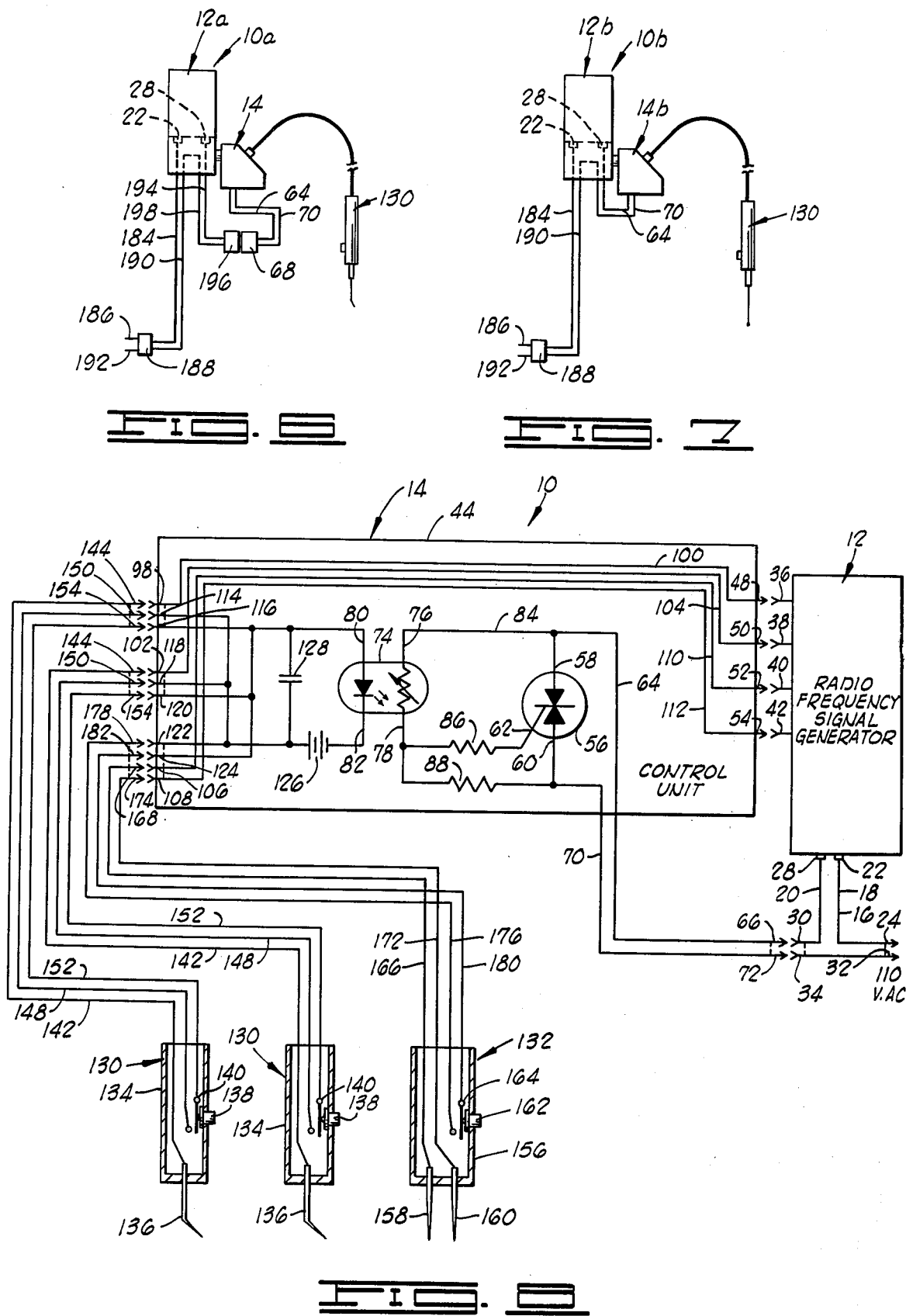

RADIO FREQUENCY CAUTERY INSTRUMENT AND CONTROL UNIT THEREFOR

BACKGROUND OF THE INVENTION

1. Field of the Invention

This invention relates generally to improvements in surgical instruments, and more particularly, but not by way of limitation, for surgical instruments employing radio frequency electrical energy in electrodesiccation, fulguration and biactive or bipolar coagulation.

2. Description of the Prior Art

The prior art comprises a number of teachings of radio frequency electrosurgical apparatus. One of the more significant developments in the field of electrosurgical apparatus is the development by the Medical Division of the Birtcher Corporation, Los Angeles, Calif., of the electrosurgical device known as the Birtcher HYFRECATOR ®. This device has received extensive acceptance by the medical community since its introduction in 1937.

A distinct disadvantage of the Birtcher HYFRECATOR ® and those other devices similar thereto, is the reliance upon foot-operated switches to activate and deactivate the signal generator during the operation of the instrument by the physician. It is deemed most advantageous to provide means for activating and deactivating the signal generator directly from the electrode assembly connected thereto. The fact that radio frequency energy is conducted directly to the electrode in the electrode assembly presents a distinct problem in designing an effective switching mechanism controlled from the electrode assembly due to the radio frequency interference induced in the switching circuitry by the radio frequency signal in the electrode.

U.S. Pat. No. 3,100,489, to R. W. Bagley, discloses a form of switching device which utilizes extensive radio frequency filtering comprising radio frequency choke coils and radio frequency filter capacitors to interconnect a switching circuit with the radio frequency operating circuit of the cautery device. This apparatus further relies on a double pole single throw electromechanical relay to effect the switching of the power circuit to the signal generator. Such a mechanism is bulky, expensive and relatively unreliable owing to the fact that the radio frequency signal is electrically connected through a filter network directly to the circuit connected to the relay. The sheer size of such a device makes it undesirable and inappropriate for use with the smaller electrosurgical devices such as the Birtcher HYFRECATOR ® and the like.

SUMMARY OF THE INVENTION

The present invention contemplates an improved radio frequency cautery instrument comprising, in combination, a radio frequency signal generator having at least one radio frequency signal output terminal and first and second electrical power input terminals, and a first power conductor for electrically connecting the first electrical power input terminal to one side of an alternating current electrical power source. The instrument further includes a voltage controlled switch having first and second main terminals and a control gate terminal with a second power conductor electrically connecting the second electrical power input terminal to the first main terminal of the voltage controlled switch. A third power conductor electrically connects the second main terminal of the voltage controlled switch and the opposite side of the alternating current electrical power source. A photon coupled isolator, having first and second control terminals and first and second main terminals, is electrically connected at the first main terminal thereof to the first main terminal of the voltage controlled switch. A first resistor interconnects the second main terminal of the photon coupled isolator and the control gate terminal of the voltage controlled switch, and a second resistor interconnects the second main terminal of the photon coupled isolator and the second main terminal of the voltage controlled switch. A radio frequency conductor having first and second ends is electrically connected at the first end thereof to the radio frequency output terminal of the radio frequency signal generator and is electrically connected at the second end thereof to a cautery electrode. An electrically insulated handle is disposed about the electrode and carries a normally open switch therein having opposite poles. A first control conductor interconnects one pole of the normally open switch and the first control terminal of the photon coupled isolator. A direct current voltage source, having a positive terminal and a negative terminal, is connected at the negative terminal thereof to the second control terminal of the photon coupled isolator. A capacitor interconnects the first control terminal of the photon coupled isolator and the positive terminal of the direct current voltage source. A second control conductor interconnects the opposite pole of the normally open switch and the positive terminal of the direct current voltage source.

An object of the invention is to increase the efficiency of radio frequency cautery instruments.

Another object of the invention is to provide an improved radio frequency cautery instrument which can be conveniently controlled from the electrode assembly thereof.

A further object of the invention is to provide a control unit to use with a radio frequency generator of a radio frequency cautery instrument which can be quickly and easily installed thereon to convert the instrument from foot control to hand control from the electrode assembly.

A still further object of the invention is to provide an economical, reliable and safe control unit for use with a radio frequency cautery instrument.

Yet another object of the present invention is to provide a radio frequency cautery instrument and control unit therefor which is economical in construction, convenient to use and reliable in operation.

Other objects and advantages of the invention will be evident from the following detailed description when read in conjunction with the accompanying drawings.

BRIEF DESCRIPTION OF THE DRAWINGS

FIG. 1 is a perspective view of the radio frequency generator of the present invention with the control unit removed therefrom.

FIG. 2 is a perspective view of the rear portion of the control unit of the present invention.

FIG. 3 is a perspective view illustrating the control unit of the present invention installed on and interconnected with the radio frequency generator.

FIG. 4 illustrates a monopolar cautery electrode assembly and connecting cable and plug for engagement with the control unit of the present invention.

FIG. 5 illustrates a bipolar cautery electrode assembly and connecting cable and cord for use with the control unit of the present invention.

FIG. 6 is a side elevation view of a slightly modified form of radio frequency signal generator and control unit installed thereon in accordance with the present invention.

FIG. 7 is a side elevation view of another slightly modified version of the radio frequency signal generator and control unit therefor installed thereon in accordance with the present invention.

FIG. 8 is a schematic diagram of the radio frequency cautery instrument and control unit therefor constructed in accordance with the present invention.

DESCRIPTION OF A PREFERRED EMBODIMENT

Referring now to the drawings, the radio frequency cautery instrument of the present invention is generally designated by the reference character 10. The instrument 10 comprises a radio frequency signal generator 12 and a control unit 14 connected thereto.

The radio frequency signal generator 12 receives its power from a conventional source of alternating current through a power cord 16 comprising a first power conductor 18 and a second power conductor 20. One end of the first power conductor 18 is electrically connected to a first electrical power input terminal 22 and the opposite end of the first power conductor is connected to one side or pole of the alternating current electrical power source by a suitable plug terminal 24 in a combination plug and socket 26. One end of the second power conductor 20 is electrically connected to a second electrical power input terminal 28 of the signal generator 12 and the opposite end of the second power conductor is connected to a socket terminal 30 in the combination plug and socket 26. A socket plug terminal 32 and second socket terminal 34 are electrically interconnected within the combined plug and socket 26.

The radio frequency signal generator 12 provides a low intensity monopolar radio frequency signal output to a first output terminal jack 36. A high intensity monopolar radio frequency output is provided to a second output terminal jack 38. The signal generator also provides a bipolar radio frequency output to a pair of bipolar output terminal jacks 40 and 42.

The control unit 14 is housed within a control unit housing 44. Extending outwardly from the back wall 46 of the housing 44 are first, second, third and fourth radio frequency input terminal plugs 48, 50, 52 and 54. These plugs are received respectively within the output terminal jacks 36, 38, 40 and 42 of the signal generator 12 to provide electrical interconnection therebetween and to support the control unit 14 upon the front wall 55 of the signal generator 12.

A voltage controlled switch 56, preferably in the form of a semiconductor device referred to as a triac, is disposed within the control unit housing 44 and includes first and second main terminals 58 and 60 and a control gate terminal 62. An electrical conductor 64 is connected at one end thereof to the first main terminal 58 and extends from the control unit housing 44 where it is electrically connected at the opposite end thereof to a plug terminal 66 of a conventional plug assembly 68. An electrical conductor 70 is connected at one end thereof to the second main terminal 60 of the triac 56 and extends from the control unit housing 44 where it is electrically connected at the opposite end thereof to a plug terminal 72 of the plug assembly 68. The plug assembly 68 is electrically connected to the combination plug and socket 26 thus electrically interconnecting plug terminal 66 and socket terminal 30 and electrically interconnecting plug terminal 72 and socket terminal 34.

A photon coupled isolator 74 is disposed within the control unit housing 44 and includes first and second main terminals 76 and 78 and first and second control terminals 80 and 82. A suitable device for employment as the photon coupled isolator 74 is the Photomod ®, Number CLM 8600 365, manufactured by Clairex Electronics, a division of Clairex Corporation, 560 South Third Avenue, Mount Vernon, N.Y. This device comprises, within a closed envelope, a light emitting diode interposed between the first and second control terminals 80 and 82 and a cadmium sulfide photoconductive cell interposed between the first and second main terminals 76 and 78. The anode of the light emitting diode is connected to the first control terminal 80 and the cathode is connected to the second control terminal 82.

An electrical conductor 84 interconnects the first main terminal 58 of the triac 56 and the first main terminal 76 at the photon coupled isolator 74. A 400 ohm, 10 watt resistor 86 interconnects the second main terminal 78 of the photon coupled isolator 74 and the control gate terminal 62 of the triac 56. A second 400 ohm, 10 watt resistor 88 interconnects the second main terminal 78 of the photon coupled isolator and the second main terminal 60 of the triac.

First and second 3-pin jacks 90 and 92 are mounted in a front wall 94 of the control unit housing 44. A 4-pin jack 96 is also mounted in the front wall 94. The first jack 90 includes a radio frequency output terminal socket 98 which is electrically connected within the housing 44 to the first radio frequency input terminal plug 48 by a conductor 100. The second jack 92 includes a radio frequency output terminal socket 102 which is electrically connected within the housing 44 to the second radio frequency input terminal plug 50 by conductor 104. The 4-pin jack 96 includes first and second radio frequency output terminal sockets 106 and 108 which are electrically connected within the housing 44 to the third and fourth radio frequency input terminal plugs 52 and 54, respectively, by conductors 110 and 112.

The jack 90 further includes a pair of switch terminal sockets 114 and 116, and the jack 92 includes a pair of switch terminal sockets 118 and 120. The 4-pin jack 96 also includes a pair of switch terminal sockets 122 and 124. The switch terminal sockets 116, 120 and 124 are mutually electrically connected to the first control terminal 80 of the photon coupled isolator 74 by means of suitable conductors. A direct current voltage source 126, preferably in the form of a conventional 9 volt battery such as manufactured by P. R. Mallory & Co., Inc. and designated as MN 1604, is disposed within the control unit housing 44 with the negative pole thereof electrically connected to the second control terminal 82 of the photon coupled isolator 74 and with the positive pole thereof mutually connected by means of suitable conductors to the switch terminal sockets 114, 118, and 122. A 0.001 microfarad, 5,000 volt capacitor 128 electrically interconnects the positive pole of the direct current voltage source 126 and the first control terminal 80 of the photon coupled isolator 74.

The present invention further includes a monopolar cautery electrode assembly 130, as shown in FIGS. 4 and 8, and a bipolar cautery electrode assembly 132, as illustrated in FIGS. 5 and 8. The monopolar cautery electrode assembly 130 comprises an electrically insulated handle 134 within which is carried a monopolar electrode 126. Various forms of monopolar electrodes can be provided and are interchangeable within the handle 134. A finger pressure-responsive switch button 138 is carried in the handle 134 and operatively engages a normally open, double-pole, single-throw switch 140 housed within the handle 134 as schematically shown in FIG. 8. A radio frequency conductor 142 is electrically connected at one end thereof to the monopolar electrode 136 and extends from the handle 134 where the opposite end thereof is electrically connected to a pin terminal 144 carried by a 3-pin plug 146. A first control conductor 148 is connected at one end thereof to one pole of the switch 140 and extends from the handle 134 to an electrical connection at the opposite end thereof with a pin terminal 150 in the plug 146. A second control conductor 152 is electrically connected at one end thereof to the other pole of the switch 140 and extends from the handle 134 to an electrical connection at the opposite end thereof with a pin terminal 154 in the plug 146.

The 3-pin plug 146 is adapted to engage either the 3-pin jack 90 or the 3-pin jack 92. When the plug 146 engages the jack 90, pin terminals 144, 150 and 154 of the plug are electrically connected to socket terminals 90, 114 and 116 of the jack, respectively. When the plug 146 is engaged with the jack 92, the pin terminals 144, 150 and 154 of the plug are electrically connected to socket terminals 102, 118 and 120 of the jack, respectively.

The bipolar cautery electrode assembly 132 comprises an electrically insulated handle 156 with a pair of bipolar electrodes 158 and 160 extending from one end of the handle 156. Various forms of bipolar electrodes can be provided and are interchangeable within the handle 156. A finger-actuated switch button 162 is mounted in the handle 156 and operatively engages a normally open, double-pole, single-throw switch 164 disposed within the handle 156. A first radio frequency conductor 166 is electrically connected at one end thereof to the bipolar electrode 158 and extends from the handle 156 to an electrical connection at the opposite end thereof to a pin terminal 168 carried by a 4-pin plug 170. A second radio frequency conductor 172 is electrically connected at one end thereof to the bipolar electrode 160 and extends from the handle 156 to an electrical connection at the opposite end thereof with a pin terminal 174 in the plug 170. A first control conductor 176 is electrically connected at one end thereof to one pole of the switch 164 and extends from the handle 156 to an electrical connection at the opposite end thereof with a pin terminal 178 in the plug 170. A second control conductor 180 is electrically connected at one end thereof to the opposite pole of the switch 164 and extends from the handle 156 to an electrical connection at the opposite end thereof to a pin terminal 182 in the plug 170. The the 4-pin plug 170 is engaged with the corresponding 4-pin jack 96, the pin terminals 168, 174, 178 and 182 of the plug 170 are electrically connected to the socket terminals 106, 108, 122 and 124 of the jack 96, respectively.

It should be noted that although two monopolar cautery electrode assemblies 130 and one bipolar cautery assembly 132 are shown connected to the control unit 14, such showing is for illustration purposes only. In actual operation of the radio frequency instrument 10, only one of the cautery electrode assemblies would be used at any given time.

FIGS. 6 and 7 illustrate slightly modified versions of the radio frequency cautery instrument of the present invention. The radio frequency cautery instrument illustrated in FIG. 6 is designated by the reference character 10a. The instrument 10a employs a modified radio frequency signal generator 12a in which the first and second power input terminals 22 and 28 thereof are housed within the signal generator 12a. One conductor 184 of an alternating current power cord extends from one pin 186 of a plug 188 and is electrically connected to the first power input terminal 22. The other conductor 190 of the power cord extends from the pin 192 of the plug 188 into the signal generator 12a. A conductor 194 extends from the second power input terminal 28 of the signal generator 12a and is electrically connected to one socket terminal of a 2-pin jack 196. A conductor 198 extends from the other socket of the jack 196 and is electrically connected within the signal generator 12a to the conductor 190. The plug terminals 66 and 72 of the plug assembly 68 are electrically connected to the sockets of the jack 196 to interconnect the control unit 14 with the radio frequency signal generator 12a.

FIG. 7 illustrates a second variation of the radio frequency instrument of the present invention which is designated by the reference character 10b. The instrument 10b includes a modified radio frequency signal generator 12b and a modified control unit 14b. The instrument 10b differs from the previously described instrument 10a in that the conductor 64 of the control unit 14b is connected directly to the second power input terminal 28 of the signal generator 12b, and the conductor 70 of the control unit 14b is electrically connected to the conductor 190 within the signal generator 12b.

OPERATION

In operation, the plug terminals 24 and 32 of the radio frequency signal generator 12 are connected to a suitable source of alternating current electrical power. The control unit 14 is electrically connected to the signal generator 12 as described above and as illustrated in FIGS. 3 and 8. A selected monopolar cautery electrode assembly 130 or bipolar cautery electrode assembly 132 is then connected to the appropriate jack 90, 92 or 96.

When it is desired to apply a radio frequency signal to the electrode or electrodes of the selected cautery electrode assembly, the operator depresses the switch button 138 or 162 to close the respective normally open switch 140 or 164 in the electrode assembly. When the normally open switch is closed, a circuit is closed thus applying the 9 volt potential of the direct current voltage source 126 across the first and second control terminals 80 and 82 of the photon coupled isolator 74 thus activating the light emitting diode thereof and directing light rays therefrom onto the cadmium sulfide photoconductive cell of the photon coupled isolator thus increasing the conductivity of the cadmium sulfide cell between the first and second main terminals 76 and 78 of the photon coupled isolator 74. The increased conductivity across the cadmium sulfide cell causes the triggering of the triac 56 thereby closing the power circuit to the radio frequency signal generator 12 and applying the full alternating current power through the triac to the radio frequency signal generator 12. When the radio frequency signal generator 12 is thus activated, a suitable radio frequency signal output is supplied thereby through the control unit 14 to the electrode or electrodes of the selected monopolar or bipolar cautery electrode assembly. The employment of the photon coupled isolator 74 isolates any radio frequency interference induced in the control conductors from the alternating current power circuit.

The radio frequency signal generator 12 is turned off by releasing pressure on the switch button thereby allowing the normally open switch to open thus breaking the circuit across the light emitting diode and reducing the conductivity of the cadmium sulfide cell which causes the triac to turn off thereby opening the power circuit to the signal generator. The capacitor 128 isolates any radio frequency transient effects from the light emitting diode when the signal generator is turned off which might otherwise damage the diode.

It will be seen from the foregoing description of the construction and operation of the present invention that the radio frequency cautery instrument described herein provides the advantage of convenient hand control of the radio frequency signal generator by the operator of the cautery electrode assembly connected thereto. The control unit 14 eliminates the requirement for the conventional foot-operated switch mechanism employed in the past for controlling such radio frequency signal generators and the problems attending the use of foot-operated switches. Typical radio frequency signal generators suitable for use with the control unit of the present invention are manufactured by the Medical Division of the Birtcher Corporation of Los Angeles, Calif. and are sold under the registered trademark "HYFRECATOR". The various forms of the present invention described above and shown in the drawings are clearly adapted for employment with and modification of the various models of the "HYFRECATOR" which are currently in existence. The control unit of the present invention is also readily acceptable for use with other radio frequency signal generators manufactured by others for use in electrodesiccation, fulguration and biactive or bipolar coagulation or the like.

Changes may be made in the combination and arrangement of parts or elements as heretofore set forth in the specification and illustrated in the drawings without departing from the spirit and scope of the invention as defined in the following claims.

What is claimed is:

1. An improved radio frequency cautery instrument, comprising in combination:
   radio frequency signal generation means having at least one radio frequency signal output terminal and first and second electrical power input terminals;
   first power conductor means for electrically connecting the first electrical power input terminal to one side of an alternating current electrical power source;
   voltage controlled switch means having first and second main terminals and a control gate terminal;
   second power conductor means for electrically connecting the second electrical power input terminal to the first main terminal of said voltage controlled switch means;
   third power conductor means for electrically connecting the second main terminal of said voltage controlled switch means to the opposite side of the alternating current electrical power source;
   photon coupled isolator means having first and second control terminals and first and second main terminals;
   electrical conductor means for electrically connecting the first main terminal of said voltage controlled switch means and the first main terminal of said photon coupled isolator means;
   first electrical resistance means for interconnecting the second main terminal of said photon coupled isolator means and the control gate terminal of said voltage controlled switch means;
   second electrical resistance means for interconnecting the second main terminal of said photon coupled isolator means and the second main terminal of said voltage controlled switch means;
   radio frequency conductor means having first and second ends for electrical connection at the first end thereof to the radio frequency signal output terminal of said radio frequency signal generation means;
   cautery electrode means electrically connected to the second end of said radio frequency conductor means;
   manually actuated switch means carried adjacent said cautery electrode means and having opposite poles;
   first control conductor means for interconnecting one pole of said manually actuated switch means and the first control terminal of said photon coupled isolator means;
   a voltage source having opposite terminals with one terminal thereof electrically connected to the second control terminal of said photon coupled isolator means; and
   second control conductor means for interconnecting the opposite pole of said manually actuated switch means and the opposite terminal of said voltage source.

2. The instrument as defined in claim 1 characterized further to include:
   an electrically insulated handle disposed adjacent said electrode means; and
   said manually actuated switch means is carried by said handle.

3. The instrument as defined in claim 1 wherein said voltage source is characterized further as being a direct current voltage source, the opposite terminals of which being positive and negative.

4. The instrument as defined in claim 1 wherein said photon coupled isolator means includes a light emitting diode connected between the first and second control terminals with the anode thereof being connected to the first control terminal and the cathode being connected to the second control terminal.

5. The instrument as defined in claim 4 wherein said voltage source is characterized further as being a direct current voltage source, the opposite terminals of which being positive and negative, the negative terminal being connected to the second control terminal of said photon coupled isolator means, and the positive terminal being connected to said second control conductor means.

6. The instrument as defined in claim 1 characterized further to include:
   electrical capacitance means interconnecting the opposite poles of said manually actuated switch means.

7. An improved radio frequency cautery instrument, comprising in combination:
   radio frequency signal generation means having at least one radio frequency signal output terminal and first and second electrical power input terminals;

first power conductor means for electrically connecting the first electrical power input terminal to one side of an alternating current electrical power source;

voltage controlled switch means having first and second main terminals and a control gate terminal;

second power conductor means for electrically connecting the second electrical power input terminal to the first main terminal of said voltage controlled switch means;

third power conductor means for electrically connecting the second main terminal of said voltage controlled switch means to the opposite side of the alternating current electrical power source;

photon coupled isolator means having first and second control terminals and first and second main terminals;

electrical conductor means for electrically connecting the first main terminal of said voltage controlled switch means and the first main terminal of said photon coupled isolator means;

first electrical resistance means for interconnecting the second main terminal of said photon coupled isolator means and the control gate terminal of said voltage controlled switch means;

second electrical resistance means for interconnecting the second main terminal of said photon coupled isolator means and the second main terminal of said voltage controlled switch means;

radio frequency conductor means having first and second ends for electrical connection at the first end thereof to the radio frequency signal output terminal of said radio frequency signal generation means;

cautery electrode means electrically connected to the second end of said radio frequency conductor means;

electrically insulated handle means disposed about the electrode means;

normally open switch means carried by said handle means and having opposite poles;

first control conductor means for interconnecting one pole of said normally open switch means and the first control terminal of said photon coupled isolator means;

a direct current voltage source having a positive terminal and a negative terminal with the negative terminal thereof electrically connected to the second control terminal of said photon coupled isolator means;

electrical capacitance means interconnecting the first control terminal of said photon coupled isolator means and the positive terminal of said direct current voltage source; and second control conductor means for interconnecting the opposite pole of said normally open switch means and the positive terminal of said direct current voltage source.

8. A control unit for use with a radio frequency cautery instrument or the like of the type which includes: a radio frequency signal generator having a radio frequency output terminal, and first and second electrical power input terminals; a first power conductor electrically interconnecting the first electrical power input terminal and one output terminal of an electrical power source; and a second power conductor having first and second ends electrically connected at the first end thereof to another output terminal of the electrical power source, said control unit comprising:

a control unit housing;

radio frequency input terminal means mounted on said housing for electrical connection with the radio frequency output terminal of the signal generator;

a voltage controlled switch disposed in said control unit housing and having first and second main terminals and a control gate terminal;

electrical conductor means for interconnecting the second electrical power input terminal to the first main terminal of said voltage controlled switch;

electrical conductor means for interconnecting the second main terminal of said voltage controlled switch and the second end of the second power conductor;

photon coupled isolator means disposed in said housing and having first and second control terminals and first and second main terminals;

electrical conductor means for interconnecting the first main terminal of said voltage controlled switch and the first main terminal of said photon coupled isolator means;

first electrical resistance means for interconnecting the second main terminal of said photon coupled isolator means and the control gate terminal of said voltage controlled switch;

second electrical resistance means for interconnecting the second main terminal of said photon coupled isolator means and the second main terminal of said voltage controlled switch;

radio frequency output terminal means mounted on said housing and electrically connected within said housing to said radio frequency input terminal means;

a pair of switch terminals mounted on said housing adjacent said radio frequency output terminal means;

first control conductor means for interconnecting the first control terminal of said photon coupled isolator means and one of said pair of switch terminals;

a direct current voltage source having two poles of opposite polarity with one of the poles electrically connected to the second control terminal of said photon coupled isolator means;

electrical capacitance means for interconnecting the opposite pole of said direct current voltage source to the first control terminal of said photon coupled isolator means;

second control conductor means for interconnecting the opposite pole of said direct current voltage source and the other of said pair of switch terminals;

cautery electrode means for electrical connection with said radio frequency output terminal means;

normally open switch means positioned adjacent said cautery electrode means for electrical connection across said pair of switch terminals;

radio frequency conductor means for connecting said cautery electrode means to said radio frequency output terminal means; and control conductor means for connecting said normally open switch means across said pair of switch terminals, whereby the closing of said normally open switch means causes said control unit to apply electrical power from the electrical power source to the radio frequency signal generator thereby supplying a radio frequency signal through said control unit to said cautery electrode means, and the opening of said normally open switch means halts the application of electrical power to the radio frequency signal generator and the radio frequency signal supplied thereby to said cautery electrode means.

9. A control unit for use with a radio frequency cautery instrument or the like of the type which includes: a radio frequency signal generator having a pair of bipolar radio frequency output terminals, and first and second electrical power input terminals; a first power conductor electrically interconnecting the first electrical power input terminal and one output terminal of an electrical power source; and a second power conductor having first and second ends electrically connected at the first end thereof to another power output terminal of the electrical power source, said control unit comprising:

a control unit housing;
first radio frequency input terminal means mounted on said housing for electrical connection with one of the pair of bipolar radio frequency output terminals of the signal generator;
second radio frequency input terminal means mounted on said housing for electrical connection with the other of the pair of bipolar radio frequency output terminals of the signal generator;
a voltage controlled switch disposed in said control unit housing and having first and second main terminals and a control gate terminal;
electrical conductor means for interconnecting the second electrical power input terminal to the first main terminal of said voltage controlled switch;
electrical conductor means for interconnecting the second main terminal of said voltage controlled switch and the second end of the second power conductor;
photon coupled isolator means disposed in said housing and having first and second control terminals and first and second main terminals;
electrical conductor means for interconnecting the first main terminal of said voltage controlled switch and the first main terminal of said photon coupled isolator means;
first electrical resistance means for interconnecting the second main terminal of said photon coupled isolator means and the control gate terminal of said voltage controlled switch;
second electrical resistance means for interconnecting the second main terminal of said photon coupled isolator means and the second main terminal of said voltage controlled switch;
first radio frequency output terminal means mounted on said housing and electrically connected within said housing to said first radio frequency input terminal means;
second radio frequency output terminal means mounted on said housing and electrically connected within said housing to said second radio frequency input terminal means;
a pair of switch terminals mounted on said housing;
first control conductor means for interconnecting the first control terminal of said photon coupled isolator means and one of said pair of switch terminals;
a direct current voltage source having two poles of opposite polarity with one of the poles electrically connected to the second control terminal of said photon coupled isolator means;
electrical capacitance means for interconnecting the opposite pole of said direct current voltage source to the first control terminal of said photon coupled isolator means;
second control conductor means for interconnecting the opposite pole of said direct current voltage source and the other of said pair of switch terminals;
bipolar cautery electrode means for electrical connection with said first and second radio frequency output terminal means;
normally open switch means positioned adjacent said bipolar cautery electrode means for electrical connection across said pair of switch terminals;
radio frequency bipolar conductor means for connecting said bipolar cautery electrode means to said first and second radio frequency output terminal means; and
control conductor means for connecting said normally open switch means across said pair of switch terminals, whereby the closing of said normally open switch means causes said control unit to apply electrical power from the electrical power source to the radio frequency signal generator thereby supplying a radio frequency signal through said control unit to said bipolar cautery electrode means, and the opening of said normally open switch means halts the application of electrical power to the radio frequency signal generator and the radio frequency signals supplied thereby to said bipolar cautery electrode means.

10. A control unit for use with a radio frequency cautery instrument or the like of the type which includes: a radio frequency signal generator having a low intensity monopolar radio frequency output terminal, a high intensity monopolar radio frequency output terminal, a pair of bipolar radio frequency output terminals, and first and second electrical power input terminals; a first power conductor electrically interconnecting the first electrical power input terminal and one output terminal of an electrical power source; and a second power conductor having first and second ends electrically connected at the first end thereof to another output terminal of the electrical power source, said control unit comprising:

a control unit housing;
first radio frequency input terminal means mounted on said housing for electrical connection with the low intensity monopolar output terminal of the signal generator;
second radio frequency input terminal means mounted on said housing for electrical connection with the high intensity monopolar output terminal of the signal generator;
third radio frequency input terminal means mounted on said housing for electrical connection with one of the pair of bipolar radio frequency output terminals of the signal generator;
fourth radio frequency input terminal means mounted on said housing for electrical connection with the other of the pair of bipolar radio frequency output terminals of the signal generator;
a voltage controlled switch disposed in said control unit housing and having first and second main terminals and a control gate terminal;

electrical conductor means for interconnecting the second electrical power input terminal to the first main terminal of said voltage controlled switch;

electrical conductor means for interconnecting the second main terminal of said voltage controlled switch and the second end of the second power conductor;

photon coupled isolator means disposed in said housing and having first and second control terminals and first and second main terminals;

electrical conductor means for interconnecting the first main terminal of said voltage controlled switch and the first main terminal of said photon coupled isolator means;

first electrical resistance means for interconnecting the second main terminal of said photon coupled isolator means and the control gate terminal of said voltage controlled switch;

second electrical resistance means for interconnecting the second main terminal of said photon coupled isolator means and the second main terminal of said voltage controlled switch;

first radio frequency output terminal means mounted on said housing and electrically connected within said housing to said first radio frequency input terminal means;

second radio frequency output terminal means mounted on said housing and electrically connected within said housing to said second radio frequency input terminal means;

third radio frequency output terminal means mounted on said housing and electrically connected within said housing to said third radio frequency input terminal means;

fourth radio frequency output terminal means mounted on said housing and electrically connected within said housing to said fourth radio frequency input terminal means;

a first pair of switch terminals mounted on said housing adjacent the first radio frequency output terminal means;

a second pair of switch terminals mounted on said housing adjacent said second radio frequency output terminal means;

a third pair of switch terminals mounted on said housing adjacent said third and fourth radio frequency output terminal means;

first control conductor means for interconnecting the first control terminal of said photon coupled isolator means and one of each of said first, second and third pairs of switch terminals;

a direct current voltage source having two poles of opposite polarity with one of the poles electrically connected to the second control terminal of said photon coupled isolator means;

electrical capacitance means for interconnecting the opposite pole of said direct current voltage source to the first control terminal of said photon coupled isolator means;

second control conductor means for interconnecting the opposite pole of said direct current voltage source and the other of each of said first, second and third pairs of switch terminals;

cautery electrode means for alternate electrical connection with said first radio frequency output terminal means and said second radio frequency output terminal means;

normally open switch means positioned adjacent said cautery electrode means for alternate electrical connection across said first pair of switch terminals and across said second pair of switch terminals;

radio frequency conductor means for connecting said cautery electrode means to said first radio frequency output terminal means and, alternately, to said second radio frequency output terminal means; and control conductor means for connecting said normally open switch means across said first pair of switch terminals and, alternately, across said second pair of switch terminals, whereby the closing of said normally open switch means causes said control unit to apply electrical power from the electrical power source to the radio frequency signal generator thereby supplying a radio frequency signal through said control unit to said cautery electrode means, and the opening of said normally open switch means halts the application of electrical power to the radio frequency signal generator and the radio frequency signal generator and the radio frequency signal supplied thereby to said cautery electrode means.

11. The control unit as defined in claim 10 characterized further to include:

bipolar cautery electrode means for electrical connection with said third and fourth radio frequency output terminal means;

normally open switch means positioned adjacent said bipolar cautery electrode means for electrical connection across said third pair of switch terminals;

radio frequency bipolar conductor means for connecting said bipolar cautery electrode means to said third and fourth radio frequency output terminal means of said control unit; and control conductor means for connecting said normally open switch means positioned adjacent said bipolar cautery electrode means across said third pair of switch terminals, whereby the closing of said normally open switch means adjacent said bipolar cautery electrode means causes said control unit to apply electrical power from the electrical power source to the radio frequency signal generator thereby supplying a radio frequency signal through said control unit to said bipolar cautery electrode means, and the opening of said normally open switch means adjacent said bipolar cautery electrode means halts the application of electrical power to the radio frequency signal generator and the radio frequency signal supplied thereby to said bipolar cautery electrode means.

12. An improved radio frequency cautery instrument comprising, in combination:

a radio frequency signal generator having at least one radio frequency signal output terminal and further having first and second electrical power input terminals;

first power conductor means electrically connecting the first electrical power input terminal to one side of an alternating current electrical power source;

voltage controlled switch means having first and second main terminals and a control gate terminal;

second power conductor means electrically connecting said second electrical power input terminal to the first main terminal of said voltage controlled switch means;

third power conductor means electrically connecting the second main terminal of said voltage controlled switch means to the opposite side of the alternating current electrical power source;

photon coupled isolator means having first and second control terminals and first and second main terminals;

electrical conductor means electrically connecting the first main terminal of said voltage controlled switch means and the first main terminal of said photon coupled isolator means;

first electrical resistance means interconnecting the second main terminal of said photon coupled isolator means and the control gate terminal of said voltage controlled switch means;

second electrical resistance means interconnecting the second main terminal of said photon coupled isolator means and the second main terminal of said voltage controlled switch means;

radio frequency conductor means having first and second ends, and electrically connected at the first end thereof to the radio frequency signal output terminal of said radio frequency signal generator;

a cautery electrode electrically connected to the second end of said radio frequency conductor means; and electrical circuit means, including a power source and a switch, connected to the first and second control terminals of said isolator means for selectively energizing and de-energizing said isolator means upon closure and opening of said switch, said switch being positioned adjacent said cautery electrode.

13. An improved radio frequency cautery instrument, comprising, in combination:

a radio frequency signal generator having at least one radio frequency signal output terminal and further having first and second electrical power input terminals;

first power conductor means electrically connecting the first electrical power input terminal to one side of an alternating current electrical power source;

voltage controlled switch means having first and second main terminals and a control gate terminal;

second power conductor means electrically connecting said second electrical power input terminal to the first main terminal of said voltage controlled switch means;

third power conductor means electrically connecting the second main terminal of said voltage controlled switch means to the opposite side of the alternating current electrical power source;

photon coupled isolator means having first and second control terminals and first and second main terminals;

electrical conductor means electrically connecting the first main terminal of said voltage controlled switch means and the first main terminal of said photon coupled isolator means;

first electrical resistance means interconnecting the second main terminal of said photon coupled isolator means and the control gate terminal of said voltage controlled switch means;

second electrical resistance means interconnecting the second main terminal of said photon coupled isolator means and the second main terminal of said voltage controlled switch means;

a cautery electrode connected to said radio frequency signal output terminal of said radio frequency signal generator for receiving radio frequency signals from said radio frequency signal generator when said voltage controlled switch means is closed to place said radio frequency signal generator in the energized power circuit including said first and second power conductor means; and electrical circuit means, including a power source and a switch, connected to the first and second control terminals of said isolator means and selectively energizing and de-energizing said isolator means upon closure and opening of said switch, said switch being positioned adjacent said cautery electrode.

* * * * *